(12) United States Patent
Torii et al.

(10) Patent No.: US 11,185,301 B2
(45) Date of Patent: Nov. 30, 2021

(54) RADIATION IMAGING APPARATUS AND RADIATION IMAGING SYSTEM

(71) Applicant: CANON KABUSHIKI KAISHA, Tokyo (JP)

(72) Inventors: Sota Torii, Kawasaki (JP); Atsushi Iwashita, Tokyo (JP); Kosuke Terui, Yokohama (JP); Akira Tsukuda, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 102 days.

(21) Appl. No.: 16/749,201

(22) Filed: Jan. 22, 2020

(65) Prior Publication Data

US 2020/0155097 A1 May 21, 2020

Related U.S. Application Data

(63) Continuation of application No. PCT/JP2018/021209, filed on Jun. 1, 2018.

(30) Foreign Application Priority Data

Aug. 4, 2017 (JP) .............................. JP2017-151760

(51) Int. Cl.
*A61B 6/00* (2006.01)
*G01N 23/04* (2018.01)

(52) U.S. Cl.
CPC ............ *A61B 6/482* (2013.01); *A61B 6/5235* (2013.01); *A61B 6/5258* (2013.01); *A61B 6/542* (2013.01);
(Continued)

(58) Field of Classification Search
CPC . G06T 5/002; G06T 5/50; G06T 2207/10116; G06T 11/008; A61B 6/482;
(Continued)

(56) References Cited

U.S. PATENT DOCUMENTS 6,125,166 A * 9/2000 Takeo .................. A61B 6/4241
378/62
7,711,082 B2 5/2010 Fujimoto
(Continued)

FOREIGN PATENT DOCUMENTS

JP S63-049142 3/1988
JP 2008-148886 A 7/2008
(Continued)

OTHER PUBLICATIONS

U.S. Appl. No. 16/103,150, Atsushi Iwashita, filed Aug. 14, 2018.
(Continued)

*Primary Examiner* — Courtney D Thomas
(74) *Attorney, Agent, or Firm* — Venable LLP

(57) ABSTRACT

A radiation imaging apparatus is provided. The apparatus comprises a detection unit configured to generate an image signal according to radiation emitted by a radiation source, an image processing unit, and a control unit. The control unit performs first imaging and second imaging performed after the first imaging using radiations of different energies, the image processing unit generates an energy subtraction image using a first image signal generated by the detection unit in the first imaging and a second image signal generated by the detection unit in the second imaging, and the second imaging is performed under a radiation irradiation condition according to a noise amount included in the first image signal.

16 Claims, 4 Drawing Sheets

(52) U.S. Cl.
CPC ....... *G01N 23/04* (2013.01); *G01N 2223/401* (2013.01)

(58) Field of Classification Search
CPC ..... A61B 6/5235; A61B 6/5258; A61B 6/542; G01N 23/04; G01N 2223/401
See application file for complete search history.

(56) References Cited

U.S. PATENT DOCUMENTS

| | | | |
|---|---|---|---|
| 7,756,240 | B2 | 7/2010 | Nishide |
| 9,048,154 | B2 | 6/2015 | Takenaka et al. |
| 9,128,196 | B2 | 9/2015 | Sato et al. |
| 9,134,432 | B2 | 9/2015 | Iwashita et al. |
| 9,234,966 | B2 | 1/2016 | Sugawara et al. |
| 9,423,512 | B2 | 8/2016 | Sato et al. |
| 9,445,030 | B2 | 9/2016 | Yagi et al. |
| 9,462,989 | B2 | 10/2016 | Takenaka et al. |
| 9,468,414 | B2 | 10/2016 | Ryu et al. |
| 9,470,800 | B2 | 10/2016 | Iwashita et al. |
| 9,470,802 | B2 | 10/2016 | Okada et al. |
| 9,541,653 | B2 | 1/2017 | Iwashita et al. |
| 9,655,586 | B2 | 5/2017 | Yagi et al. |
| 9,737,271 | B2 | 8/2017 | Iwashita et al. |
| 9,812,474 | B2 | 11/2017 | Yagi et al. |
| 9,820,711 | B2 | 11/2017 | Tsukuda |
| 9,971,046 | B2 | 5/2018 | Ryu et al. |
| 9,989,656 | B2 | 6/2018 | Sato et al. |
| 10,009,990 | B2 | 6/2018 | Takenaka et al. |
| 10,070,082 | B2 | 9/2018 | Tsukuda |
| 10,197,684 | B2 | 2/2019 | Terui et al. |
| 10,274,612 | B2 | 4/2019 | Ishii et al. |
| 10,441,238 | B2 | 10/2019 | Terui et al. |
| 2011/0216883 | A1* | 9/2011 | Tsukamoto .......... A61B 6/4241 378/62 |
| 2014/0239186 | A1 | 8/2014 | Sato et al. |
| 2014/0361189 | A1 | 12/2014 | Kameshima et al. |
| 2016/0270755 | A1 | 9/2016 | Takenaka et al. |
| 2018/0128755 | A1 | 5/2018 | Iwashita et al. |
| 2018/0317868 | A1 | 11/2018 | Terui et al. |
| 2018/0328862 | A1 | 11/2018 | Sato et al. |
| 2019/0179036 | A1 | 6/2019 | Takenaka et al. |
| 2019/0320993 | A1 | 10/2019 | Noda et al. |
| 2019/0349541 | A1 | 11/2019 | Iwashita et al. |
| 2020/0124749 | A1 | 4/2020 | Takenaka et al. |
| 2020/0150059 | A1* | 5/2020 | Torii .................... A61B 6/5258 |

FOREIGN PATENT DOCUMENTS

| | | |
|---|---|---|
| JP | 2009-82174 A | 4/2009 |
| JP | 2009-131464 A | 6/2009 |
| JP | 2009-131564 | 6/2009 |
| JP | 2010-284350 A | 12/2010 |

OTHER PUBLICATIONS

U.S. Appl. No. 16/731,143, Kosuke Terui, filed Dec. 31, 2019.
U.S. Appl. No. 16/745,807, Sota Torii, filed Jan. 17, 2020.
U.S. Appl. No. 16/813,970, Atsushi Iwashita, filed Mar. 10, 2020.
U.S. Appl. No. 16/847,074, Akira Tsukuda, filed Apr. 13, 2020.

* cited by examiner

F I G. 1
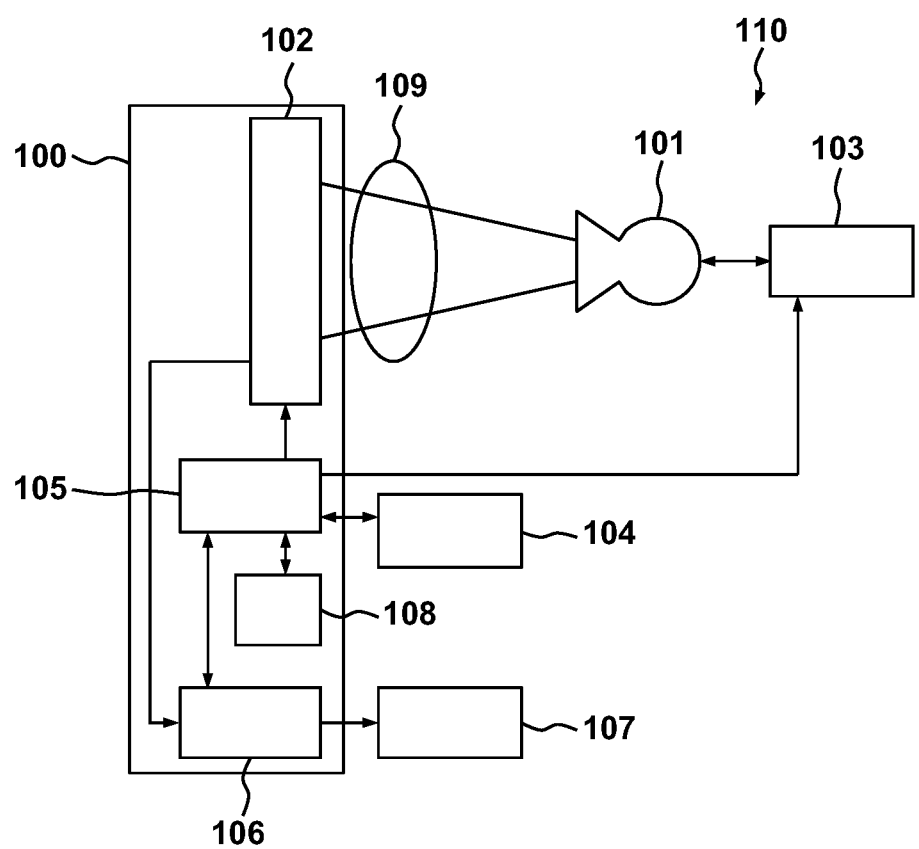

FIG. 2

```
START
  ↓
SET IMAGING CONDITIONS — S201
  ↓
CAPTURE HIGH-ENERGY IMAGE — S202
  ↓
CAPTURE LOW-ENERGY IMAGE — S203
  ↓
GENERATE ENERGY SUBTRACTION IMAGE — S204
  ↓
DISPLAY IMAGES — S205
  ↓
END
```

FIG. 3

| BODY THICKNESS | IMAGING CONDITION | |
|---|---|---|
| | HIGH-ENERGY IMAGE | LOW-ENERGY IMAGE |
| THIN | 140kV 10mA 10ms | 100kV 50mA 20ms |
| NORMAL | 140kV 10mA 20ms | 100kV 70mA 40ms |
| THICK | 140kV 10mA 40ms | 100kV 90mA 80ms |

RADIATION IMAGING APPARATUS AND RADIATION IMAGING SYSTEM

CROSS-REFERENCE TO RELATED APPLICATIONS

This application is a Continuation of International Patent Application No. PCT/JP2018/021209, filed Jun. 1, 2018, which claims the benefit of Japanese Patent Application No. 2017-151760, filed Aug. 4, 2017, both of which are hereby incorporated by reference herein in their entirety.

BACKGROUND OF THE INVENTION

Field of the Invention

The present invention relates to a radiation imaging apparatus and a radiation imaging system.

Background Art

In medical image diagnosis or nondestructive inspection, a radiation imaging apparatus using a flat panel detector (FPD) made of a semiconductor material is widely used. One known imaging method using an FPD is a method of acquiring an energy subtraction image using radiations of different energy components. PTL 1 shows a radiation imaging apparatus using a DXA (Dual X-ray Absorptiometry) method that repetitively irradiates an object with high-energy radiation and low-energy radiation and performs imaging. Generally, in an object with a thick body, the detection value (count) of radiation at the time of low-energy radiation imaging is much smaller than the count of radiation at the time of high-energy radiation imaging, as compared to an object of an average physical constitution. PTL 1 shows that to equalize the counts of radiations detected in imaging using high-energy radiation and low-energy radiation, the ratio of the times over which low-energy radiation and high-energy radiation are repetitively alternately generated by a radiation generation unit is controlled.

CITATION LIST

Patent Literature

PTL 1: Japanese Patent Laid-Open No. 2009-131564

In PTL 1, control is performed to make the time over which low-energy radiation higher than that of high-energy radiation, thereby equalizing the counts of detected radiations. However, even if the counts of detected radiations equal, a noise amount included in a high-energy radiation image and that in a low-energy radiation image can be different. Noise included in an energy subtraction image can depend on the noise amount of the radiation image obtained using high-energy radiation and that in the radiation image obtained using low-energy radiation. To improve the quality of the energy subtraction image, the noise amount included in the high-energy image and the noise amount included in the low-energy image need to be taken into consideration.

It is an object of the present invention to provide a technique advantageous in improving the quality of an energy subtraction image in a radiation imaging apparatus.

SUMMARY OF THE INVENTION

According to some embodiments, a radiation imaging apparatus comprising a detection unit configured to generate an image signal according to radiation emitted by a radiation source, an image processing unit, and a control unit, wherein the control unit performs first imaging and second imaging performed after the first imaging using radiations of different energies, the image processing unit generates an energy subtraction image using a first image signal generated by the detection unit in the first imaging and a second image signal generated by the detection unit in the second imaging, and the second imaging is performed under a radiation irradiation condition according to a noise amount included in the first image signal, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 is a view showing an example of the arrangement of a radiation imaging system using a radiation imaging apparatus according to an embodiment of the present invention.

FIG. 2 is a flowchart showing the procedure of imaging of an energy subtraction image using the radiation imaging apparatus shown in FIG. 1.

FIG. 3 is a view showing an example of radiation irradiation conditions in imaging of the energy subtraction image shown in FIG. 2.

DESCRIPTION OF THE EMBODIMENTS

Figure 4:
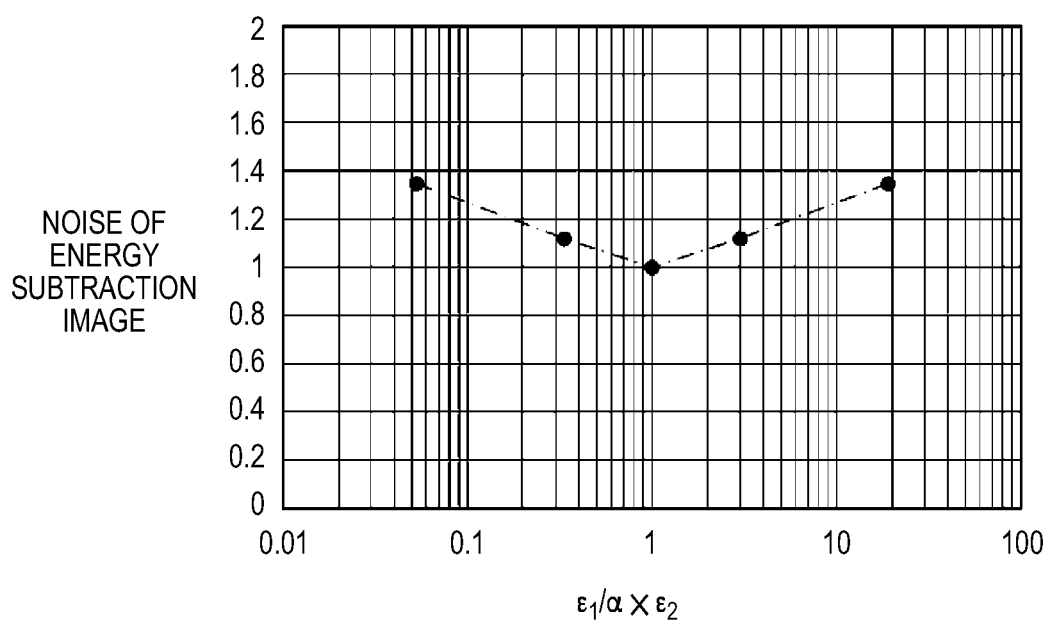
FIG. 4 is a view showing the relationship between noise in a high-energy image and a low-energy image and noise in an energy subtraction image.

Detailed embodiments of a radiation imaging apparatus according to the present invention will now be described with reference to the accompanying drawings. Radiation according to the present invention can include not only α-rays, β-rays, and γ-rays that are beams generated by particles (including photons) emitted by radioactive decay but also beams having equal or more energy, for example, X-rays, particle rays, and cosmic rays.

The arrangement and operation of a radiation imaging apparatus according to an embodiment of the present invention will be described with reference to FIGS. 1 to 4. FIG. 1 is a view showing an example of the arrangement of a radiation imaging system 110 using a radiation imaging apparatus 100 according to the first embodiment of the present invention. The radiation imaging system 110 is configured to electrically capture an optical image converted from radiation to obtain an electrical signal (image signal) used to generate a radiation image. The radiation imaging system 110 includes, for example, the radiation imaging apparatus 100, a radiation source 101, an exposure control unit 103, an imaging condition setting unit 104, and an image display unit 107. The radiation imaging apparatus 100 includes, for example, a detection unit 102, an image processing unit 106, and a control unit 105 configured to control the constituent elements of the radiation imaging apparatus 100.

The radiation source 101 irradiates an object 109 with radiation. The radiation source 101 includes a radiation generation unit (tube bulb) that generates radiation, and a collimator that defines the beam divergence angle of the radiation generated by the radiation generation unit. The exposure control unit 103 controls the dose of radiation emitted by the radiation source 101. The detection unit 102 detects radiation that enters through the object 109, and generates an image signal. The control unit 105 controls the detection unit 102 based on a signal output from the imaging condition setting unit 104. In addition, the control unit 105 controls irradiation of radiation from the radiation source 101 via the exposure control unit 103. The imaging condition setting unit 104 can be a computer configured to input an imaging condition such as a radiation irradiation condition used to capture a radiation image by a user, or a display that displays an input imaging condition or the like. The image processing unit 106 generates an energy subtraction image using a plurality of image signals output from the detection unit 102. In the arrangement shown in FIG. 1, an example in which the imaging condition setting unit 104 is arranged outside the radiation imaging apparatus 100 is shown. However, some or all of the functions of the imaging condition setting unit 104 may be provided in the radiation imaging apparatus 100. Additionally, in the arrangement shown in FIG. 1, an example in which the image processing unit 106 is arranged in the radiation imaging apparatus 100 is shown. However, some or all of image processes performed by the image processing unit 106 may be performed by another image processing unit arranged outside the radiation imaging apparatus 100. The image display unit 107 can be a monitor such as a display that displays image data output from the image processing unit 106.

Processing from image capturing of an object to display of an energy subtraction image will be described next with reference to FIG. 2. A case in which the energy subtraction image is acquired using a two-shot method will be described here. However, adaptation to an imaging method such as a one-shot method other than the two-shot method is also possible.

First, in step S201, radiation irradiation conditions at the time of imaging, such as the irradiation dose of radiation and the tube voltage and the tube current of the radiation source 101, are set in accordance with a user operation on the imaging condition setting unit 104. In this case, in accordance with the conditions of the object such as the constituent substance and the thickness of the object, the user may select the radiation irradiation conditions from combinations of radiation irradiation conditions used in two imaging operations set in advance. Hence, as shown in FIG. 1, the radiation imaging apparatus 100 may include a storage unit 108 that stores in advance the combinations of radiation irradiation conditions used in two imaging operations performed in the two-shot method. In addition, to select the combination of radiation irradiation conditions, imaging of an object may be performed in advance using a low dose, and an object thickness or the like may be estimated from the transmission dose. In this case, the control unit 105 may select an appropriate combination of radiation irradiation conditions based on the estimated object thickness and the like.

FIG. 3 shows an example of combinations of radiation irradiation conditions used in imaging. The radiation irradiation conditions include, for example, the values of the tube voltage and the tube current of the radiation source 101, which decide the energy value of radiation, and a radiation irradiation time (the charge accumulation time in the detection unit 102). The combinations of the irradiation conditions can be created in accordance with, for example, a noise amount assumed to be included in an image signal. Here, the object is a human body. However, the object need not always be a human body. For example, objects may be classified by materials such as an organic compound, a light metal, and a heavy metal, and the combinations of radiation irradiation conditions may be held in the storage unit 108. Furthermore, if the object is a compound, functions may be provided such that the user inputs the information of the thickness to the imaging condition setting unit 104 based on the above-described classification, and the control unit 105 selects recommended radiation irradiation conditions from the storage unit 108 and sets the conditions.

When the radiation irradiation conditions are selected, in step S202, the control unit 105 captures a radiation image under radiation irradiation conditions for a high-energy image in synchronism with the exposure control unit 103. Next, in step S203 as well, a radiation image is captured under radiation irradiation conditions for a low-energy image, as in step S202. In this embodiment, imaging is performed first using high-energy radiation, and imaging using low-energy radiation is then performed. However, the order is not limited to this. Imaging by low-energy radiation may be performed first, and imaging by high-energy radiation may be performed later.

After imaging is performed twice using radiations of different energies, in step S204, an energy subtraction image is generated. More specifically, the image processing unit 106 generates an energy subtraction image using an image signal generated by the detection unit 102 in the imaging using the high-energy radiation and an image signal generated by the detection unit 102 in the imaging using the low-energy radiation. Next, in step S205, the energy subtraction image output from the image processing unit 106, the high-energy image and the low-energy image before energy subtraction processing, and the like are displayed on the image display unit 107. The user can perform diagnosis or the like using the images displayed on the image display unit 107.

A method of creating the combinations of the radiation irradiation conditions shown in FIG. 3 will be described next in detail. The noise amount of the energy subtraction image after four arithmetic operations of the high-energy image and the low-energy image can be calculated by equations (1), (2), and (3) below. Here, $M_1$ is the pixel value of the high-energy image, $\varepsilon_1$ is the noise value of the high-energy image, $M_2$ is the pixel value of the low-energy image, and $\varepsilon_2$ is the noise value of the low-energy image.

$$(M_1 \pm \varepsilon_1) \pm (M_2 \pm \varepsilon_2) = (M_1 \pm M_2) \pm \sqrt{\varepsilon_1^2 + \varepsilon_2^2} \qquad (1)$$

$$(M_1 \pm \varepsilon_1) \times (M_2 \pm \varepsilon_2) = (M_1 \times M_2) \pm \sqrt{(M_2 \times \varepsilon_1)^2 + (M_1 \times \varepsilon_2)^2} \qquad (2)$$

$$(M_1 \pm \varepsilon_1)/(M_2 \pm \varepsilon_2) = \left(\frac{M_1}{M_2}\right) \pm \sqrt{\left(\frac{1}{M_2} \times \varepsilon_1\right)^2 + \left(\frac{M_1}{M_2^2} \times \varepsilon_2\right)^2} \qquad (3)$$

In this specification, a case in which bone suppression processing is performed as representative processing of energy subtraction processing will be described. Bone suppression processing is image processing of removing a bone portion from a radiation image obtained using a low-energy image and a high-energy image. In bone suppression processing, generally, image processing is often performed using equation (4). Here, $M_{cor}$ is the pixel value of the energy subtraction image, $\varepsilon_{cor}$ is the noise value of the energy subtraction image, I is the irradiation dose of radiation, and α is a correction coefficient (constant) used to add a weight to the high-energy image and the low-energy image.

$$M_{cor} \pm \varepsilon_{cor} = (M_1 \pm \varepsilon_1) - \alpha \times (M_2 \pm \varepsilon_2) \quad (4)$$

By applying equation (1) to equation (4), the noise value $\varepsilon_{cor}$ of the energy subtraction image is given by (5).

$$\varepsilon_{cor} = \sqrt{\varepsilon_1^2 + (\alpha \times \varepsilon_2)^2} \quad (5)$$

According to the relational expression (inequality (6)) of arithmetic geometric mean, to minimize the noise value $\varepsilon_{cor}$ of the energy subtraction image in equation (5), equation (7) needs to be satisfied.

$$\varepsilon_1^2 + (\alpha \times \varepsilon_2)^2 \geq 2\alpha \varepsilon_1 \varepsilon_2 \quad (6)$$

$$\varepsilon_1^2 = (\alpha \times \varepsilon_2)^2 \quad (7)$$

That is, equation (8) below needs to be satisfied.

$$\varepsilon_1 = \alpha \times \varepsilon_2 \quad (8)$$

$$\varepsilon \propto \sqrt{I} \quad (9)$$

Expression (9) represents that since the number of arriving radiation particles complies with a Poisson distribution, noise in the radiation image is proportional to the square root of the transmission dose. Here, when reducing only noise in the energy subtraction image without increasing the exposure dose of the object is considered, it is possible to obtain radiation irradiation conditions using expressions (7) and (9). However, the noise values $\varepsilon_1$ and $\varepsilon_2$ representing the noise amounts of the high-energy image and the low-energy image change for each thickness or substance of the object. For this reason, imaging cannot necessarily be performed under ideal radiation irradiation conditions. Hence, the combination of radiation irradiation conditions is created such that, for example, $\varepsilon_1/(\alpha \times \varepsilon_2)$ falls within the range of ⅓ to 3. In other words, imaging using low-energy radiation is performed under radiation irradiation conditions such that the noise amount of the image signal of imaging using low-energy radiation to which the correction coefficient is applied becomes ⅓ times or more and 3 times or less of the noise amount of the image signal of imaging using high-energy radiation. FIG. 4 is a graph showing the transition of the noise amount of the energy subtraction image with respect to the noise amount of the low-energy image and the noise amount of the high-energy image. As is apparent from FIG. 4, if the setting can be done such that $\varepsilon_1/(\alpha \times \varepsilon_2)$ falls within the range of ⅓ to 3, the increase of the noise amount can be suppressed to about 10% or less from the optimum noise amount of the energy subtraction image. As described above, the combination of radiation irradiation conditions may be set based on the relational expressions (equations (1), (2), and (3)) of error propagation in four arithmetic operations.

In this embodiment, a form in which processing of separating a bone image and a soft tissue image is performed by performing, for example, differential processing for the low-energy image and the high-energy image has been described. However, the present invention is not limited to this form. For example, the processing can also be applied to a case in which a bone image and a soft tissue image are separated by solving nonlinear simultaneous equations using the low-energy image and the high-energy image or a case in which an electron density image and an effective atomic number image are separated.

Additionally, in this embodiment, the energy value of radiation is changed by changing the tube voltage and the tube current of the radiation source 101. However, the present invention is not limited to this. For example, images by radiations of different energies may be acquired based on the presence/absence of insertion of a beam hardening filter or the like without changing the tube voltage and the tube current of the radiation source 101.

In this embodiment, the combination of radiation irradiation conditions is selected such that imaging using low-energy radiation is performed under radiation irradiation conditions according to the noise amount included in the image signal generated by imaging using high-energy radiation. This can suppress noise of an energy subtraction image and acquire an energy subtraction image of high quality.

Figure 5:
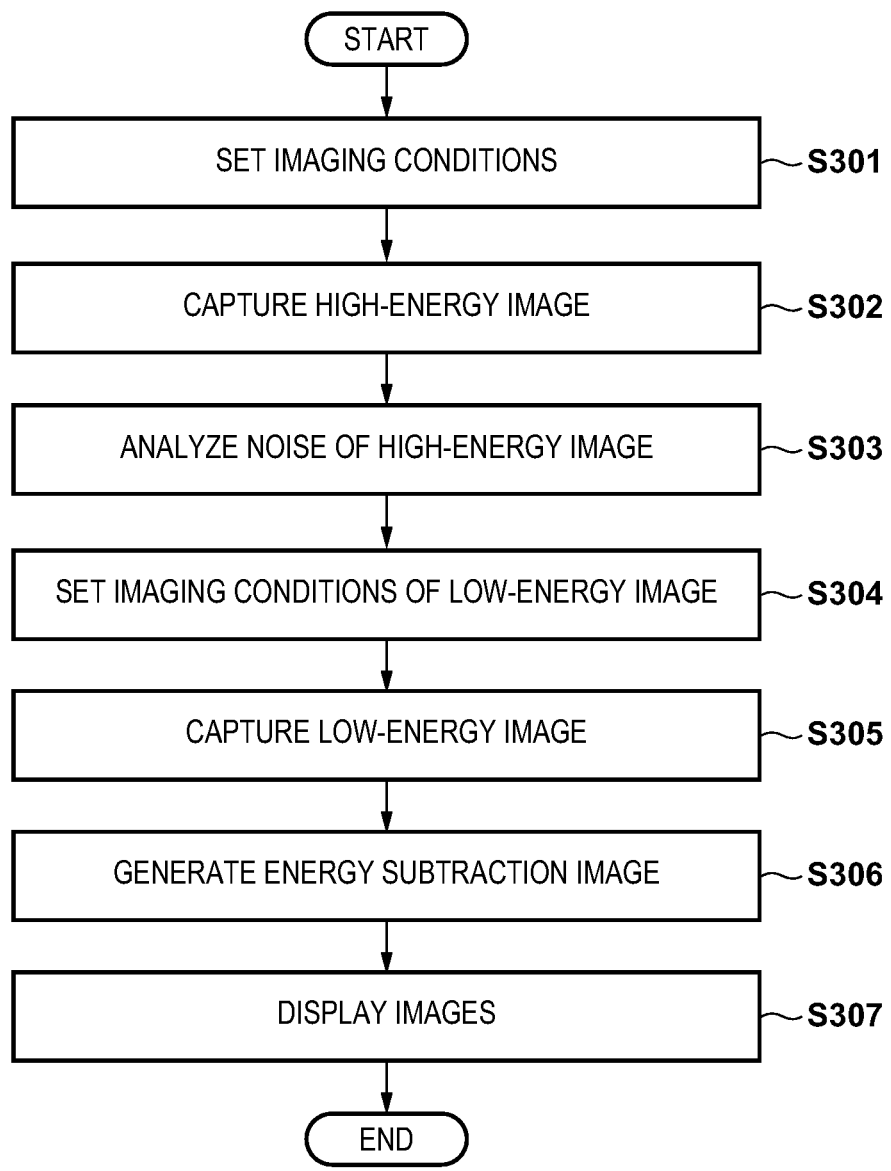
FIG. 5 is a flowchart showing the procedure of imaging of an energy subtraction image using the radiation imaging apparatus shown in FIG. 1.

The arrangement and operation of a radiation imaging apparatus according to an embodiment of the present invention will be described with reference to FIG. 5. FIG. 5 is a flowchart of processing from image capturing of an object to display of an energy subtraction image using a radiation imaging apparatus 100 according to the second embodiment of the present invention. The radiation imaging apparatus 100 and a radiation imaging system 110 can be similar to those of the above-described first embodiment, and a description thereof will be omitted here.

First, in step S301, radiation irradiation conditions at the time of imaging, such as the energy value of radiation such as the tube voltage and the tube current of a radiation source 101 and a radiation irradiation time (the charge accumulation time in a detection unit 102) are set in accordance with a user operation on an imaging condition setting unit 104. In this case, in accordance with the conditions of the object such as the constituent substance and the thickness of the object, the user sets the radiation irradiation conditions of at least the imaging operation (in this embodiment, imaging of a high-energy image using high-energy radiation) performed first in two imaging operations. At this time, as shown in FIG. 1, the radiation imaging apparatus 100 may include a storage unit 108 that stores in advance radiation irradiation conditions to be used in the first imaging operation. If the radiation imaging apparatus 100 includes the storage unit 108, in accordance with the object, the user may select appropriate conditions from the radiation irradiation conditions stored in the storage unit 108. In addition, the radiation imaging apparatus 100 may include a camera or a gauge used to measure the thickens of the object. In this case, in accordance with information such as the detected thickness of the object, a control unit 105 may select appropriate conditions from the radiation irradiation conditions stored in the storage unit 108. In addition, to select the radiation irradiation conditions, imaging of the object may be performed in advance using a low dose, the object thickness or the like may be estimated from the transmission dose, and the control unit 105 may decide appropriate radiation irradiation conditions based on the estimated object thickness or the like.

After the radiation irradiation conditions of the high-energy image are set in step S301, in step S302, imaging of a high-energy image using high-energy radiation is performed. The image signal of the captured high-energy image is output from the detection unit 102 to an image processing unit 106. In step S303, the control unit 105 analyzes the noise amount included in the image signal of the high-energy image acquired and output to the image processing unit 106 in step S302. As for a region of interest to analyze the noise amount, the image signal of a predetermined region in the detection unit 102 may be analyzed. The control unit 105 may select the image signal of an arbitrary portion of the detection unit 102 using a region extraction technique or the like. For example, the control unit 105 may select, as the predetermined region, a region with a small transmission dose, such as a lumbar spine where a bone thickness is large. Additionally, for example, an appropriate filter or the like may be arranged in the visual field of the detection unit 102, and the user may select, as the predetermined region, the place where the filter is arranged. If a filter or the like is arranged in the visual field, the control unit 105 may recognize the place where the filter is arranged as a region with a small transmission dose and select it as the predetermined region. The control unit 105 performs processing of, for example, obtaining the standard deviation (noise) of the image signal of the predetermined region in the image signal of the high-energy image, thereby deciding the noise amount included in the image signal of the high-energy image.

In step S304, based on the noise amount decided from the analysis result of the noise amount included in the high-energy image in step S303, the control unit 105 decides radiation irradiation conditions of imaging of a low-energy image using low-energy radiation. As the radiation irradiation conditions of imaging of the low-energy image, the control unit 105 may decide both the energy value (the tube voltage, the tube current, and the like) of radiation in the imaging using low-energy radiation and the radiation irradiation time. In addition, the control unit 105 may select appropriate radiation irradiation conditions from the radiation irradiation conditions stored in the storage unit 108, thereby deciding the radiation irradiation conditions of the low-energy image. Additionally, for example, in step S301, temporary radiation irradiation conditions (the energy value of radiation and the radiation irradiation time) of imaging of the low-energy image are selected in advance. Then, in step S304, the control unit 105 may correct at least one of an energy value of radiation and the radiation irradiation time in the temporary radiation irradiation conditions in accordance with the decided noise amount, thereby deciding the radiation irradiation conditions of the low-energy image. The radiation irradiation conditions at the time of imaging of the low-energy image are obtained by a method similar to that of the above-described first embodiment such that the noise amount of an energy subtraction image is made small or minimized if possible. As described above, in this embodiment as well, the radiation irradiation conditions of the low-energy image are decided based on the relational expressions (equations (1), (2), and (3)) of error propagation in four arithmetic operations.

After the radiation irradiation conditions of the low-energy image are decided, in step S305, the control unit 105 controls the detection unit 102 and an exposure control unit 103 and performs imaging of the low-energy image using low-energy radiation. At this time, the irradiation dose of radiation may be controlled using an AEC (Auto Exposure Control) function of stopping radiation irradiation at a desired transmission dose or a photo timer. In this case, when the transmission dose of a region set in advance by the user or the like reaches a desired dose, the control unit 105 may output, to the exposure control unit 103, a signal to stop radiation irradiation from the radiation source 101. In accordance with the signal, the exposure control unit 103 controls the radiation source 101 to stop radiation irradiation.

In step S306, the image processing unit 106 performs energy subtraction processing using the image signal of the high-energy image and the image signal of the low-energy image output from the detection unit 102. In step S307, an energy subtraction image obtained by the energy subtraction processing is output from the image processing unit 106 and displayed on an image display unit 107. At this time, not only the energy subtraction image but also the high-energy image and the low-energy image may be output from the image processing unit 106 to the image display unit 107 and displayed.

In this embodiment, imaging using high-energy radiation is performed first, and imaging using low-energy radiation is performed later. However, the imaging order is not limited to this. Additionally, in the above-described embodiments, an example in which imaging is performed twice is shown. However, imaging may be performed three or more times, and energy subtraction processing may be performed.

In this embodiment, the noise amount included in the image signal generated by imaging using high-energy radiation is decided. After that, setting of the radiation irradiation conditions of imaging using low-energy radiation is done in accordance with the noise amount. This can suppress noise of an energy subtraction image and acquire an energy subtraction image of high quality.

The above-described means provides a technique advantageous in improving the quality of an energy subtraction image in a radiation imaging apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
a detector configured to generate an image signal according to radiation emitted by a radiation source;
a controller configured to perform first imaging and second imaging performed after the first imaging using radiations of different energies; and
an image processor configured to generate an energy subtraction image using a first image signal generated by the detector in the first imaging and a second image signal generated by the detector in the second imaging, wherein
the controller is configured to decide a noise amount included in the first image signal based on an image signal of a predetermined region of the first image signal in the first imaging, decide a radiation irradiation condition of the second imaging in accordance with the noise amount, and perform the second imaging under the decided radiation irradiation condition.

2. The radiation imaging apparatus according to claim 1, wherein the radiation irradiation conditions used in the first imaging and the second imaging include energy values of radiations and radiation irradiation times in the first imaging and the second imaging.

3. The radiation imaging apparatus according to claim 1, wherein the radiation irradiation conditions used in the first imaging and the second imaging are set based on a relational expression of error propagation in four arithmetic operations.

4. The radiation imaging apparatus according to claim 1, wherein the controller is configured to decide the noise amount included in the first image signal based on a standard deviation of an image signal of a predetermined region of the first image signal in the first imaging.

5. The radiation imaging apparatus according to claim 1, wherein the controller is configured to decide at least one of an energy value of radiation and the radiation irradiation time in the second imaging as the radiation irradiation condition of the second imaging.

6. The radiation imaging apparatus according to claim 1, wherein the radiation imaging apparatus further comprises a storage unit configured to store in advance radiation irradiation conditions used in the first imaging, and
the radiation irradiation condition of the first imaging is selected, in accordance with an object, from the radiation irradiation conditions stored in the storage unit.

7. The radiation imaging apparatus according to claim 6, wherein the radiation irradiation condition used in the first imaging includes an energy value of radiation and a radiation irradiation time in the first imaging.

8. The radiation imaging apparatus according to claim 6, wherein the storage unit is configured to store the radiation irradiation condition used in the second imaging, and
the controller is configured to correct, in accordance with the noise amount, a temporary radiation irradiation condition selected before the second imaging, thereby deciding the radiation irradiation condition of the second imaging.

9. The radiation imaging apparatus according to claim 1, wherein the controller is configured to use, as the image signal of the predetermined region, an image signal of a region with a small transmission dose in the first image signal.

10. The radiation imaging apparatus according to claim 1, wherein the radiation irradiation condition of the second imaging is decided based on a relational expression of error propagation in four arithmetic operations.

11. The radiation imaging apparatus according to claim 1, wherein the image processor is configured to apply a correction coefficient to the second image signal when generating the energy subtraction image, and
the second imaging is performed under a radiation irradiation condition in which the noise amount of the second image signal to which the correction coefficient is applied becomes $\frac{1}{3}$ to 3 times the noise amount of the first image signal.

12. The radiation imaging apparatus according to claim 1, wherein an energy value of radiation in the first imaging is higher than the energy value of radiation in the second imaging.

13. A radiation imaging system, comprising:
the radiation imaging apparatus according to claim 1; and
a radiation source configured to emit radiation.

14. The radiation imaging apparatus according to claim 1, wherein the controller is configured to perform the first imaging using a radiation irradiation condition decided in accordance with information including a thickness of an object, and
decide the radiation irradiation condition of the second imaging in accordance with the information including the thickness of the object and the noise amount.

15. The radiation imaging apparatus according to claim 14, wherein the information including the thickness of the object further includes information of a constituent substance of the object.

16. A control method of a radiation imaging apparatus comprising a detector configured to generate an image signal according to radiation emitted by a radiation source, the method comprising the steps of:
generating a first image signal by the detector in a first imaging;
generating a second image signal by the detector in a second imaging using radiation of a different energy than that of the first imaging; and
generating an energy subtraction image using the first and second image signals, wherein
a noise amount included in the first image signal is decided based on an image signal of a predetermined region of the first image signal in the first imaging,
a radiation irradiation condition of the second imaging is decided in accordance with the noise amount, and
the second imaging is performed under the decided radiation irradiation condition.

* * * * *